United States Patent [19]

Chen-Wu et al.

[11] Patent Number: 5,288,415
[45] Date of Patent: Feb. 22, 1994

[54] APPARATUS AND METHOD FOR SEPARATION OF BIOLOGICAL AGENTS

[76] Inventors: Joan L.-P. Chen-Wu; Jing-Jung Chen, both of 464 Commonwealth Ave., Boston, Mass. 02215

[21] Appl. No.: 826,775

[22] Filed: Jan. 28, 1992

[51] Int. Cl.$^5$ ............................................. B01D 21/26
[52] U.S. Cl. ................................. 210/781; 210/360.1; 435/30; 435/311; 435/312
[58] Field of Search .................. 210/232, 360.1, 360.2, 210/361, 335–338, 781, 787, 789, 321.6, 489, 321.84, 804; 494/36, 37, 20; 604/406, 408–410; 422/101; 436/177, 178

[56] References Cited

U.S. PATENT DOCUMENTS 5,047,004  9/1991  Wells ...................................... 494/20
5,178,602  1/1993  Wells ...................................... 494/37

Primary Examiner—Joseph W. Drodge

[57] ABSTRACT

An assembly for the separation by centrifugal force of biological agents from a suspension, which assembly includes (1) a first compartment including a first filtering means as a part of its surface, the first filtering means having pores capable of allowing the passage of the biological agents therethrough; and (2) a second compartment for receiving the biological agents that pass through the pores, the first compartment and the second compartment being securely attached together in such a manner that the spacial relationship among the first compartment, the second compartment, and the first filtering means remain the same throughout centrifugation of the assembly.

8 Claims, 4 Drawing Sheets

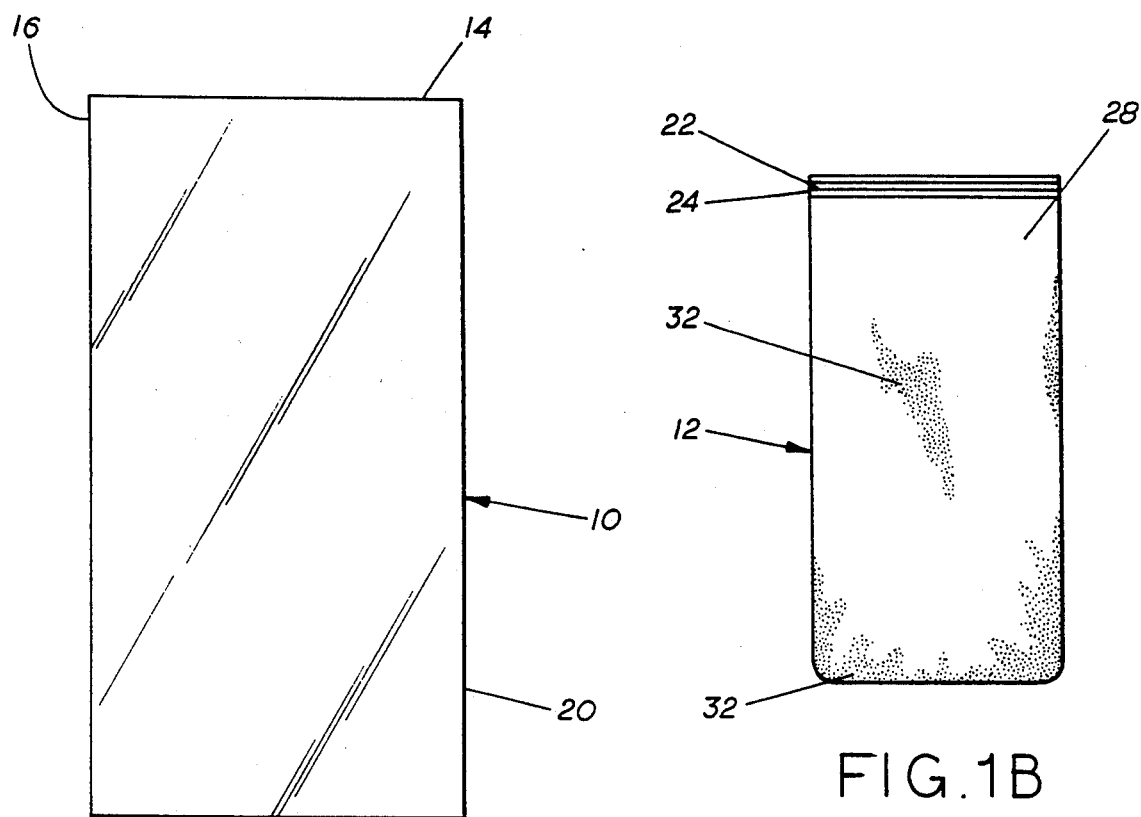
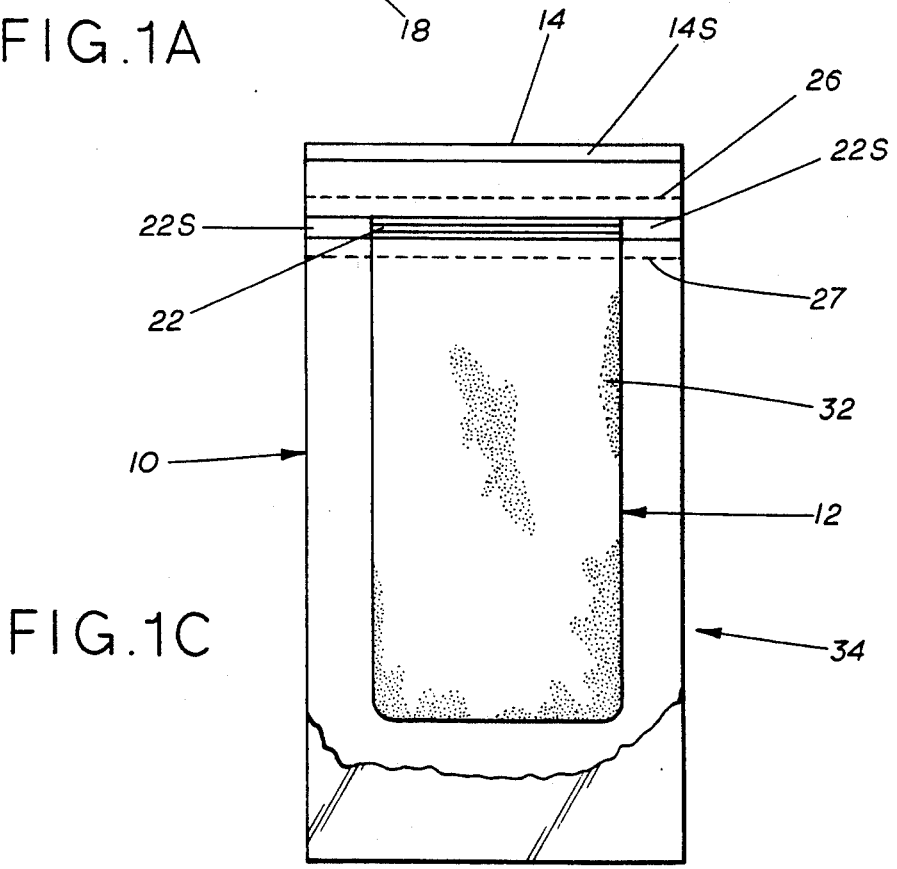

APPARATUS AND METHOD FOR SEPARATION OF BIOLOGICAL AGENTS

FIELD OF THE INVENTION

The present invention relates generally to an apparatus or method for separation and collection of biological agents in a suspension.

BACKGROUND OF THE INVENTION

Before the amounts and identities of biological agents (e.g., bacteria, fungus, insects, parasites or mammalian cells) in a sample, such as food, soil or a clinical specimen, can be determined, several steps must first be performed.

As an initial step, the sample is usually suspended in a proper buffer, followed by blending or "stomaching" to release the biological agents from the sample. Stomaching was first introduced about twenty years ago [Sharp, A. N. et al., Appl. Microbiol. 24:175-178 (1972) and has since become a useful alternative to blending in the preparation of foods for microbiological analysis.

The biological agents in the sample suspension are thereafter separated from the sample by filtration. The biological agents in the filtrate are most of the time far too diluted, entailing the need of enrichment (i.e., growth of the biological agents) to increase the number of the agents.

Enrichment is a time-consuming process and may take as long as 2 weeks for certain types of biological agents. Also, contamination may occur during the enrichment process. Furthermore, it renders reliable quantification of the biological agents almost impossible.

SUMMARY OF THE INVENTION

In general, one aspect of the invention features an assembly for the separation by centrifugal force of biological agents from a suspension, which assembly comprises (1) a first compartment including a first filtering means as a part of its surface, the first filtering means having pores capable of allowing the passage of the biological agents therethrough; and (2) a second compartment for receiving the biological agents that pass through the pores, the first compartment and the second compartment being securely attached together in such a manner that the spacial relationship among the first compartment, the second compartment, and the first filtering means remain the same throughout centrifugation of the assembly.

In a preferred embodiment, the above-described assembly further comprises an inlet means for allowing introduction of the suspension into the first compartment. Preferably, the inlet means includes a zip-seal device. It is particularly preferred that the assembly also contains one or more additional filtering means which are disposed in the first compartment and spaced from the first filtering means, and have pores larger than those of the first filtering means.

In a preferred assembly, the first and second compartments are plastic bags which are dimensioned and disposed so that the former is suspended in the latter when the assembly is in an upright position, the wall of the inner plastic bag including the first filtering means.

Alternatively, the assembly may be a detachable centrifuge tube that can be detached into a top tubular part and a bottom tubular part, the top tubular part including a porous disc device securely affixed therein and serving to compartmentalize the centrifuge tube into a top chamber and a bottom chamber. If desired, the top tubular part may be detachable into two or more tubular subparts, with each subpart containing one porous disc device, with the device at the upper position more porous than that at the lower position. It is preferable that the tubular parts are threadedly engaged. Alternatively, a snap-on design can also be used to put the tubular parts together.

Another feature of the present invention features a device for the separation by centrifugal force of biological agents in a suspension, which device comprises (1) a centrifuge tube; and (2) one or more filtering means having pores capable of allowing the passage of biological agents therethrough and being securely affixed in the centrifuge tube as to compartmentalize the centrifuge tube into two or more compartments, whereby the one or more filtering means remain motionless relative to the centrifuge tube during centrifugation of the device. Preferably, the device further comprises a means for allowing introduction of the suspension into the top compartment and another means for providing access to the bottom compartment.

Also contemplated within the invention is a process for separating and collecting biological agents from a suspension, which process comprises the steps of (1) introducing the suspension into a first chamber having pores capable of allowing the passage of the biological agents therethrough; (2) separating the biological agents from other particulate materials in the suspension by forcing them to pass through the pores; and (3) collecting the separated biological agents as a pellet at the bottom of a second chamber; wherein the separating step and the collecting step are performed simultaneously.

It is preferable that in the above process the biological agents in the suspension to be collected are bacteria, fungus, insects, parasites, or mammalian cells.

It is also preferable that in the above process the separating step and the collecting step are effected by filtration with the aid of centrifugal force.

Further, the process may comprise the additional step of removing the filtrate from the second chamber after the separating step, so that only the pellet remains therein. If necessary, the pellet can be resuspended after the removing step.

Advantages of the present invention are numerous. For example, in the plastic bag embodiment, solid samples can be blended in the inner bag with an appropriate buffer in a stomaching machine. More importantly, the invention provides a rapid method for collecting biological agents in a suspension, since the biological agents are separated from other undesired materials and packed together as a rather firm pellet at the same time. Furthermore, according to some embodiments of the invention, it is not necessary to transfer the sample from one container to another, thus greatly reducing the likelihood of contamination. In addition, since no such transfer is required, the recovery yield of the biological agents is high; as a result, one may be able to eliminate the need of subsequent enrichment of the collected biological agents. As mentioned above, enrichment is time-consuming and contamination-prone.

BRIEF DESCRIPTION OF THE DRAWINGS

The above and further advantages of the invention may be better understood by referring to the following description in conjunction with the accompanying drawings, in which, FIG. 1 is a diagrammatic representation showing a side elevation of an embodiment of the invention, which contains an outer plastic bag (FIG. 1A) and an inner plastic bag (FIG. 1B). FIG. 1C shows an assembly of the outer and inner plastic bags.

In all the drawings, identical numbers represent identical or similar elements. Various elements shown in the drawing are not necessarily in proportion to their actual sizes.

Figure 2:
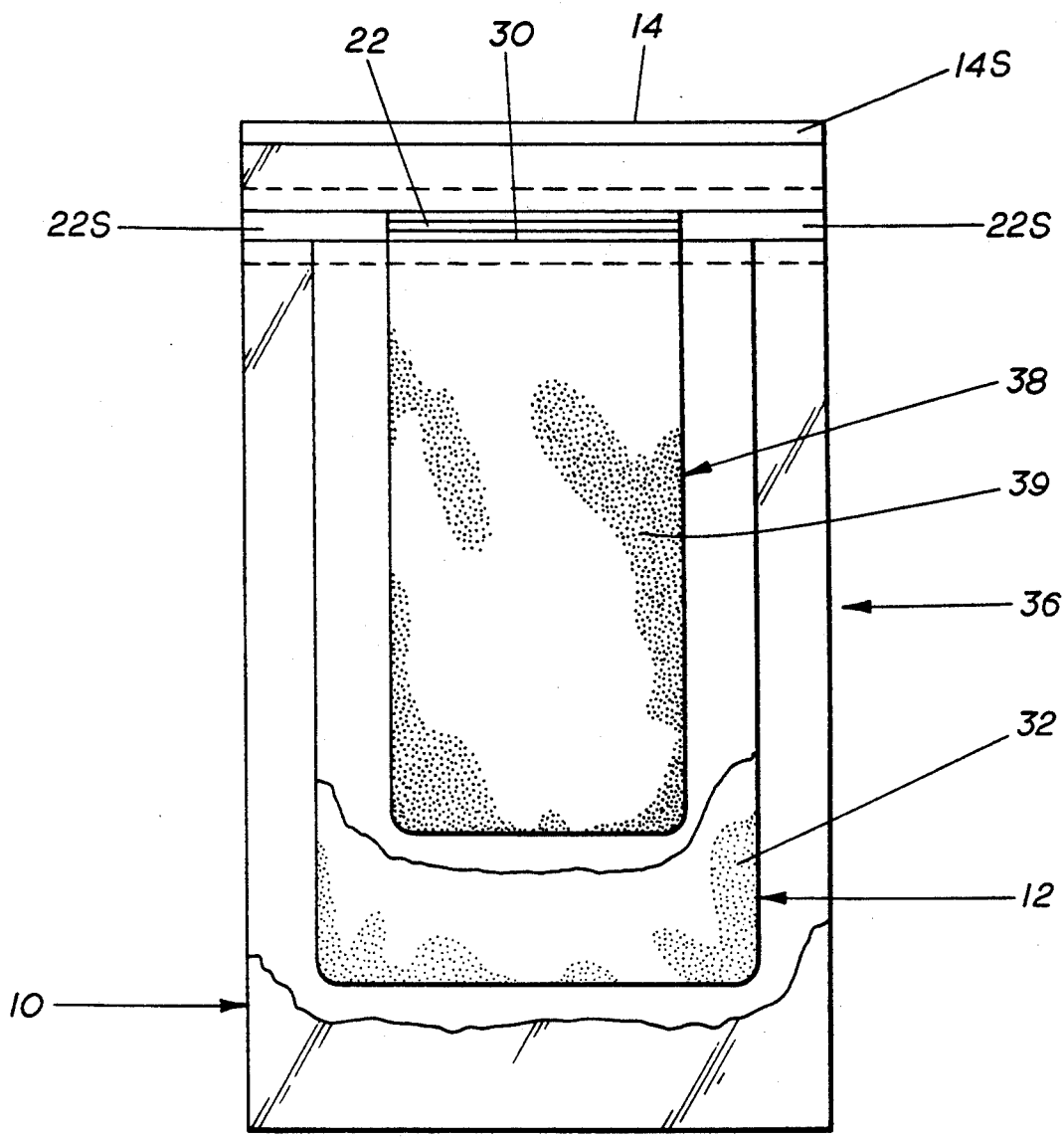
FIG. 2 is a diagrammatic representation showing a side elevation of a variation of the FIG. 1 embodiment.

Further, as used herein the terms such as "inner", "outer", "top", "bottom", "lower", "suspend", "upright", "horizontal" and the like, as used herein, are intended only to denote relative direction solely with reference to the figures in the accompanying drawings.

DETAILED DESCRIPTION OF THE PREFERRED EMBODIMENTS

Apparatus

Refer first to FIGS. 1A and 1B which show two transparent and pliant plastic bags, i.e., outer bag 10 and inner bag 12. The two bags 10 and 12 are both of rectangular shape and dimensioned so that the former is large enough to accommodate the latter. The outer bag 10 has an open top edge 14 and is otherwise sealed on its other three edges 16, 18 and 20. The inner bag 12, on the other hand, has a zip-seal device 22 near its top edge 24. Both bags 10 and 12 must endure the magnitude of centrifugation force to be applied thereto and can be made of materials such as polypropylene, nylon or polyethylene.

The surface 28 of the inner bag 12 contains pores 32 of such a size as to allow passage of biological agents to be separated or collected and exclusion most unwanted larger particulate materials. The suitable pore size for collection of a specific biological agent can be readily determined by a person of ordinary skill in the art without undue experimentation.

The zip-seal device is well known in the art of plastic bag manufacture. Briefly, it includes a groove as an integral part of a plastic sheet and a protruding ridge as an integral part of another plastic sheet. The groove and the ridge are dimensioned and disposed in such a manner so that they snugly mate with each other. Provision of such a device in a plastic bag allows one to open and close the plastic bag conveniently.

FIG. 1C shows an assembly 34 in which the inner bag 12 is securely affixed to the internal upper surfaces of the outer bag 10 via both sides near its top edges 24, i.e., around the external surfaces of the inner bag 12 opposing the groove and the ridge of the zip-seal device 22, respectively. As a result, the inner bag 12 is suspended from the upper portion of the outer bag 10 when the assembly 34 is in an upright position. For reasons to be explained later, it is preferable that both the areas 14s immediately below the edge 14 and the areas 22s flanking the zip-seal device 22 in the outer bag 10 be sealed so that the entire assembly 34 becomes hermetical.

The assembly 34 is in fact a centrifuge bag. Note that the distance between the bottom of inner bag 12 and the bottom of the outer bag 10 is to be determined by the volume of the suspension to be introduced into the assembly 34, or the volume of the filtrate in the outer bag 10 after centrifugation. More specifically, the level of the filtrate in the outer bag 10 should not be above the bottom of the inner bag 12 throughout centrifugation of the assembly 34.

FIG. 2 shows an assembly 36, which is a variation of the FIG. 1C assembly 34. The assembly 36, which can be constructed in a manner similar to that employed in constructing the assembly 34 as described above, differs from the assembly 34 in that it contains an additional porous bag 38, which is smaller than, and suspended within, the inner bag 12 when the assembly 34 is in an upright position. The additional porous bag 38, like the inner bag 12, contains pores 39 in its surface. The pores 39 of the bag 38 are larger in size than those in the inner bag 12. A zip-seal device 22 is provided near the top edge 30 of the bag 38. The areas flanking the zip-seal device 22 is preferably sealed, so that the zip-seal device 22 constitutes the sole inlet to the bag 38.

Figure 3C:
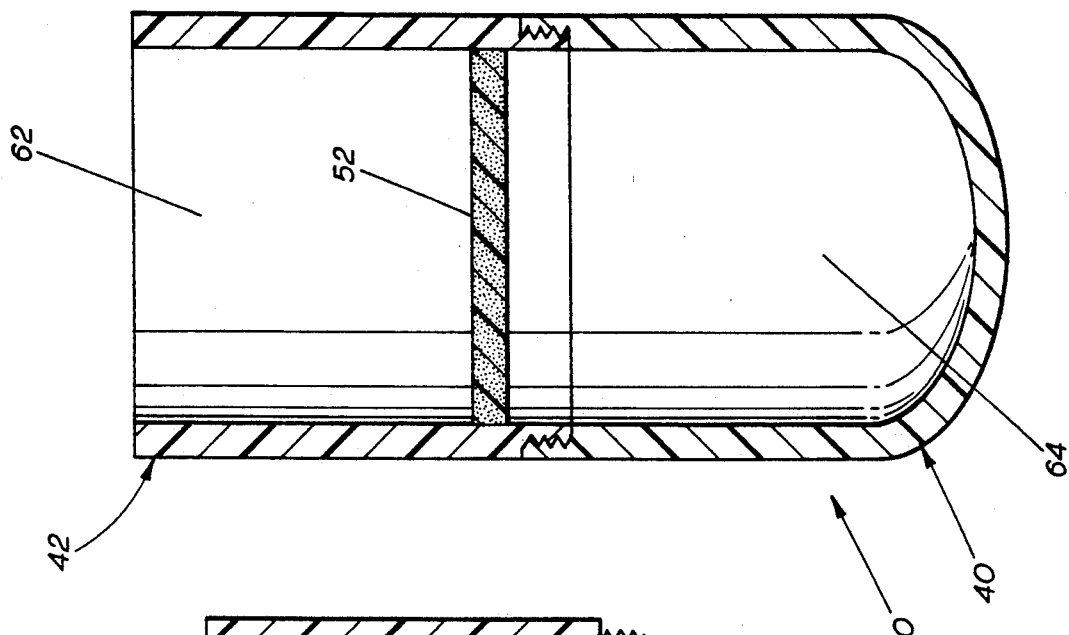
FIG. 3C shows an assembly of the top and bottom tubular parts.
Figure 3B:
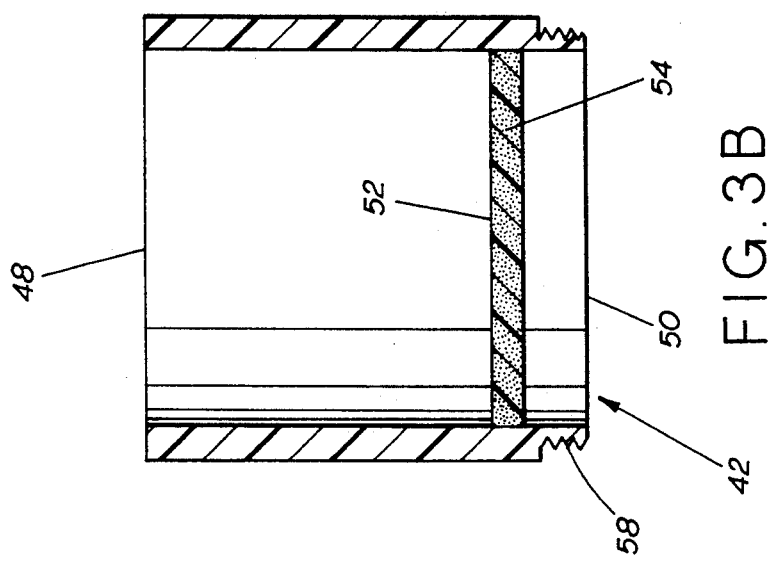
FIG. 3 is a cross-sectional side elevation view of an embodiment of the invention, which contains a top tubular part (FIG. 3A) and a bottom tubular part (FIG. 3B).
Figure 3A:
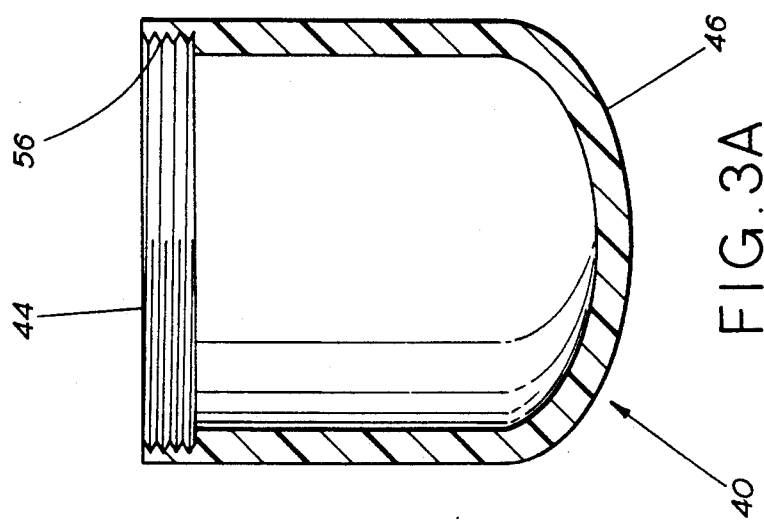

Refer now to FIGS. 3A, 3B and 3C. FIGS. 3A and 3B show two tubular parts 40 and 42. The term "tubular" used herein only refers to a cylindrical, hollow construction without implication as to its length.

The tubular part 40 (FIG. 3A) has an open top end 44 and a closed bottom end 46. The tubular part 42 (FIG. 3B), on the other hand, are open at both ends 48 and 50. Furthermore, it is securely fitted with a porous disc device 52 with pores 54 capable of allowing the passage of biological agents to be separated or collected. The tubular parts may be made of materials such as polypropylene and polyethylene. The porous disc device 52, on the other hand, are filtration screens made of materials such as nylon, polyethylene, polypropylene, fluorocarbon and polyester. As to the size of the pores 54, see discussion above regarding the pores 12 of the inner bag 28 in the FIG. 1 embodiment.

The disc device 52 shown in FIG. 3B is an integral unit of rigid construction. Alternatively, the disc device 52 may be composed of a filter membrane and a rigid grid on top of which the membrane is placed. The pore size of the filter membrane, which is smaller than that of the grid, is so dimensioned as to prevent or greatly reduce passage therethrough of particulates larger than the biological agents of interest.

The upper, outer portion 56 of the tubular part 40 and the lower, inner portion 58 of the tubular part 42 are properly threaded so that the two parts 40 and 42 can be threadedly engaged to each other to form an assembly 60 (FIG. 3C), i.e, a centrifuge tube 60 fitted with a porous disc device 52 which compartmentalizes it into a upper chamber 62 and a lower chamber 64. The volume of the lower chamber is so dimensioned as to accommodate the filtrate after centrifugation.

Figure 4:
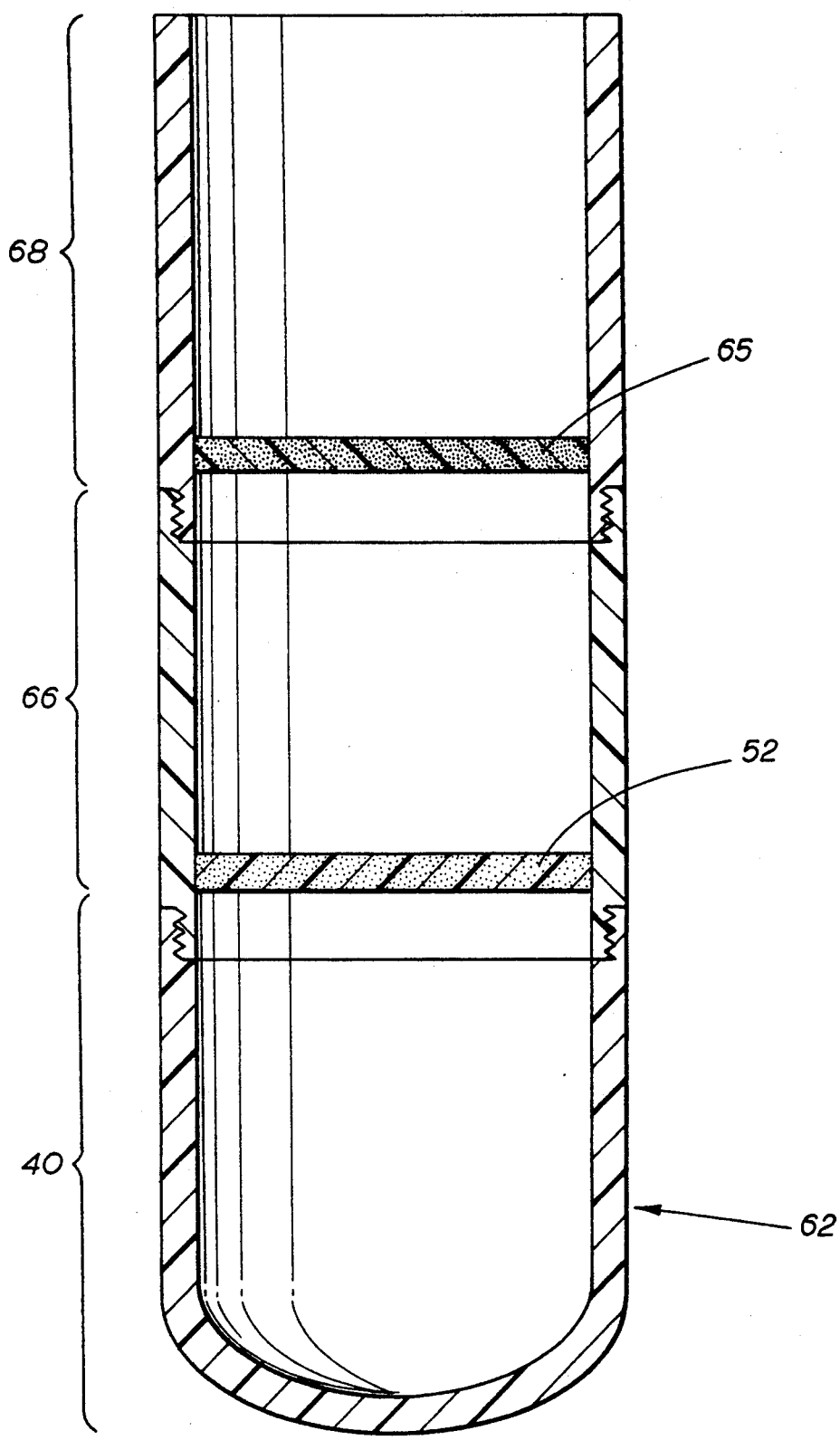
FIG. 4 is a cross-sectional side elevation view of a variation of the FIG. 3 embodiment.

FIG. 4 shows another assembly 62, which is a variation of the FIG. 3C assembly 60. The assembly 62 differs from the assembly 60 only in that it contains an additional porous disc device 65, which is securely affixed above, and has a pore size larger than that of, the porous disc device 52. The assembly 62 is composed of three tubular parts: the bottom part 40, the middle part 66 and the top part 68. All three parts 40, 66 and 68 can be secured together by threaded engagement. Both of the tubular parts 66 and 68 are fitted with the porous disc devices 52 and 65, respectively.

Use

Two types of embodiments have been described above, i.e., the embodiments of a centrifuge bag (i.e., FIGS. 1C, and 2) and the embodiments of a centrifuge tube (i.e., FIGS. 3C and 4). In many situations, it is preferable that any of the embodiments disclosed herein be sterilized before use. Since the FIGS. 1C and 2 assemblies are sealed, they can be pre-sterilized by the manufacturers and remain sterile at all times without the need for any special care.

To demonstrate how to employ the embodiments of the present invention to collect biological agents in a suspension, the detailed steps involved in using the centrifuge bag 34 (FIG. 1C) and the centrifuge tube 60 (FIG. 3C) are set forth below.

Before using the centrifuge bag 34, its outer bag 10 must first be opened by removing its top portion by cutting along a tear line 26 (FIG. 1C). The zip-seal device 22 is then unlocked. Thereafter, a proper amount of a suspension that might contain biological agents is poured into the inner bag 32 through the opening, followed by immediate closing of the zip-seal device 22. Note that, since areas 22s in the assembly 34 are sealed, any accidental, undesired spilling of the suspension into the outer bag 12 is rendered impossible. Also note that solid samples can be stomached in the centrifuge bag 34, since the bags 10 and 12 are pliant.

The suspension-containing centrifuge bag is subsequently centrifuged at a proper speed for a proper length of time, so that it does not only facilitate passage of the biological agents of interest through the porous membrane of the inner bag 12, it also forcibly packs the biological agents together to form a rather firm pellet at the bottom of the outer bag 10. The centrifuge bag 34 can be clamped in a centrifuge tube adaptor so that it is securely positioned in the centrifuge tube during the centrifugation. The centrifugation force to be applied and the duration of centrifugation depend on the type of biological agents to be collected and can be readily determined by a person of ordinary skill in the art. It is to be noted that the provision of the zip-seal device 22 enables one to perform centrifugation with the sample hermetically sealed, thereby preventing or reducing any undesired contamination.

The pellet thus formed can be readily retrieved by conducting the following steps: (1) detach the inner bag 12 by cutting along another tear line 27 (FIG. 1C), (2) remove the detached inner bag 12, and (3) remove the supernatant in the outer bag 10. Care must be taken during this process so that the pellet is not disturbed. The pellet can then be resuspended in a proper buffer for subsequent analysis.

Similar steps can be followed when the assembly 60 is used, except that there is no cutting is involved in gaining an access to the upper chamber 62 or the lower chamber 64. More specifically, after centrifugation, the supernatant in the lower chamber 64 can be readily removed by disengaging the top tubular part 42 and the bottom tubular part 40.

Note that both the FIGS. 3C and 4 assemblies is reusable, since all of their parts, including the porous disc device, are readily accessible upon detachment and thus can be thoroughly washed.

At times, provision of one or more additional filtering devices may be necessary to prevent clogging or to expedite the collection process. For example, when the FIGS. 2 and 4 embodiments are used, a sample suspension is first passed through a more porous filtering device to remove those particulate materials which are especially large. The use of the FIGS. 2 and 4 embodiments is otherwise similar to what has been described below.

The foregoing description of specific embodiments of this invention is not meant to be limiting. Instead, it will be apparent that variations and modifications may be made to the invention, with the attainment of some or all of the advantages of the invention.

For example, an additional zip-seal device may be provided below the tear line 27 in the outer bag 10 of the FIG. 1C or FIG. 2 embodiment, so that, after removal of the inner bag(s) 12 and 38, the pellet or the its suspension in the outer bag 10 can be conveniently sealed.

Other embodiments with such variations and modifications also come within the scope of the invention.

What is claimed is:

1. An assembly adapted for separation by centrifugal force of biological agents from a suspension, which assembly comprises:
   a first compartment including first filtering means as a part of its surface, said first filtering means having pores capable of allowing passage of said biological agents therethrough; and
   a second compartment, which is in communication only with said first compartment via said filtering means, for receiving said biological agents that pass through said pores, said first compartment and said second compartment being securely attached together in such a manner that the spacial relationship among said first compartment, said second compartment, and said first filtering means remain the same throughout centrifugation of said assembly,
   wherein said first compartment and said second compartment are defined by a first plastic bag and a second plastic bag which are dimensioned and disposed so that said first plastic bag is suspended in said second plastic bag when said assembly is in an upright position, the wall of said first plastic bag including said first filtering means.

2. The assembly of claim 1, further comprising one or more additional plastic bags, said one or more additional plastic bags being disposed in said first plastic bag spaced from said first filtering means and having pores larger than those of said first filtering means.

3. The assembly of claim 1, further comprising an inlet means to said first compartment which includes a zip-seal device.

4. A process for separating and collecting biological agents from a suspension, which process comprises the steps of:
   introducing said suspension into a first chamber having pores capable of allowing passage of said biological agents therethrough;
   separating said biological agents from other particulate materials in said suspension by forcing them to pass through said pores; and
   collecting said separated biological agents as a pellet at the bottom of a second chamber; wherein said separating step and said collecting step are performed simultaneously by filtration with the aid of centrifugal force.

5. The process of claim 4, wherein said biological agents are selected from the group consisting of bacteria, fungus, insects, parasites and mammalian cells.

6. The process of claim 4, further comprising the step of removing the filtrate from said second chamber after said separating step.

7. The process of claim 6, wherein said biological agents are selected from the group consisting of bacteria, fungus, insects, parasites and mammalian cells.

8. The process of claim 6, further comprising the step of resuspending said pellet after said removing step.

* * * * *